US011906435B2

(12) United States Patent
Brueckner et al.

(10) Patent No.: US 11,906,435 B2
(45) Date of Patent: Feb. 20, 2024

(54) SYSTEM INCLUDING AUTO-ALIGNMENT

(71) Applicant: ATONARP INC., Tokyo (JP)

(72) Inventors: Lukas Brueckner, Nieder-Olm (DE); David Anderson, Fremont, CA (US)

(73) Assignee: ATONARP INC., Tokyo (JP)

( * ) Notice: Subject to any disclaimer, the term of this patent is extended or adjusted under 35 U.S.C. 154(b) by 0 days.

(21) Appl. No.: 18/001,772

(22) PCT Filed: Sep. 10, 2021

(86) PCT No.: PCT/JP2021/033382
§ 371 (c)(1),
(2) Date: Dec. 14, 2022

(87) PCT Pub. No.: WO2022/054921
PCT Pub. Date: Mar. 17, 2022

(65) Prior Publication Data
US 2023/0194430 A1  Jun. 22, 2023

Related U.S. Application Data

(60) Provisional application No. 63/077,080, filed on Sep. 11, 2020.

(51) Int. Cl.
*G01J 3/44* (2006.01)
*G01N 21/65* (2006.01)
*A61B 5/1455* (2006.01)

(52) U.S. Cl.
CPC .......... *G01N 21/65* (2013.01); *A61B 5/1455* (2013.01); *G01N 2021/653* (2013.01)

(58) Field of Classification Search
CPC .......... G01N 21/65; G01N 21/636; G01N 2021/653; G01N 2021/655;
(Continued)

(56) References Cited

U.S. PATENT DOCUMENTS

2007/0070349 A1* 3/2007 Harris ............... G01J 3/36
356/417
2012/0050733 A1* 3/2012 Takimoto ........... G02B 21/16
356/343
(Continued)

FOREIGN PATENT DOCUMENTS

JP  2007278783 A  10/2007
WO  2006021929 A1  3/2006

OTHER PUBLICATIONS

International Preliminary Report on Patentability (PCT/IPEA/409) issued in corresponding International Patent Application No. PCT/JP2021/033382 dated Sep. 16, 2022. (4 pages).
(Continued)

*Primary Examiner* — Uzma Alam
*Assistant Examiner* — Jonathon Cook
(74) *Attorney, Agent, or Firm* — BUCHANAN INGERSOLL & ROONEY PC

(57) ABSTRACT

A system including a signal obtaining module and a controller is provided. The signal obtaining module includes: a receiver to which an emission light generated in the target by an excitation light is input; a receiving optical path that guides the emission light and a residual light, which is at least a part of the excitation light propagated forward, coaxially between the target and the receiver; a separator that separates the residual light from the receiving optical path to be routed to an image sensor; and an actuator for controlling an optical relative position between the target and the receiver. The controller includes a module that controls the actuator to maintain an optical alignment.

14 Claims, 4 Drawing Sheets

(58) Field of Classification Search
CPC .... G01N 2021/656; G01J 3/44; G01J 3/4406; G01J 3/4412; G01J 3/443; G01J 3/0237; G01J 3/0289
See application file for complete search history.

(56) References Cited

U.S. PATENT DOCUMENTS

| | | |
|---|---|---|
| 2014/0028996 A1* | 1/2014 | Liu ........................ G01J 3/0237 356/51 |
| 2015/0316533 A1 | 11/2015 | Kerimo et al. |
| 2017/0089836 A1 | 3/2017 | Kato et al. |
| 2019/0033192 A1 | 1/2019 | Masuya et al. |
| 2020/0011831 A1* | 1/2020 | Wang .................... G01J 3/0294 |
| 2020/0025677 A1* | 1/2020 | Prater .................... G01J 3/427 |
| 2020/0103276 A1* | 4/2020 | Olivo .................... G01J 3/0237 |
| 2020/0233195 A1 | 7/2020 | Day et al. |
| 2020/0271300 A1 | 8/2020 | Guo et al. |

OTHER PUBLICATIONS

International Search Report (PCT/ISA/210) and Written Opinion (PCT/ISA/237) dated Nov. 30, 2021, by the Japanese Patent Office as the International Searching Authority for International Application No. PCT/JP2021/033382. (7 pages).

* cited by examiner

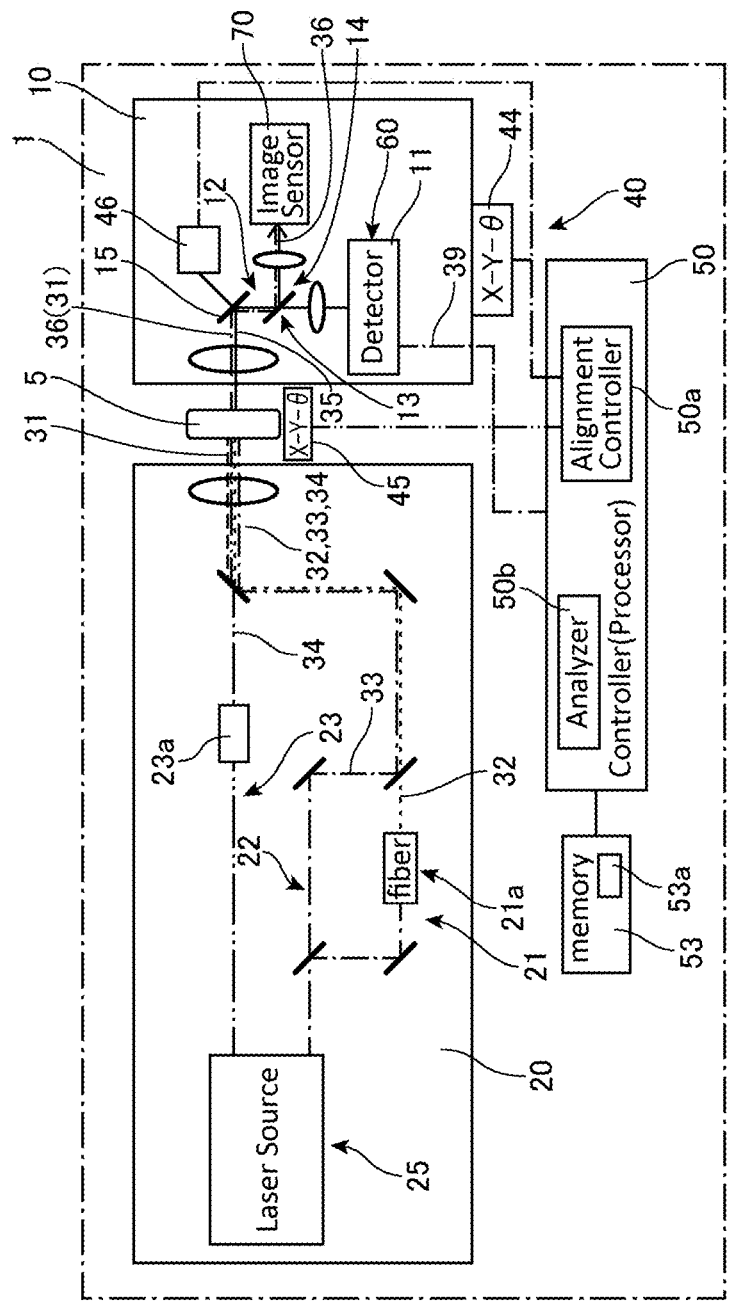
[Fig. 1]

[Fig. 2]
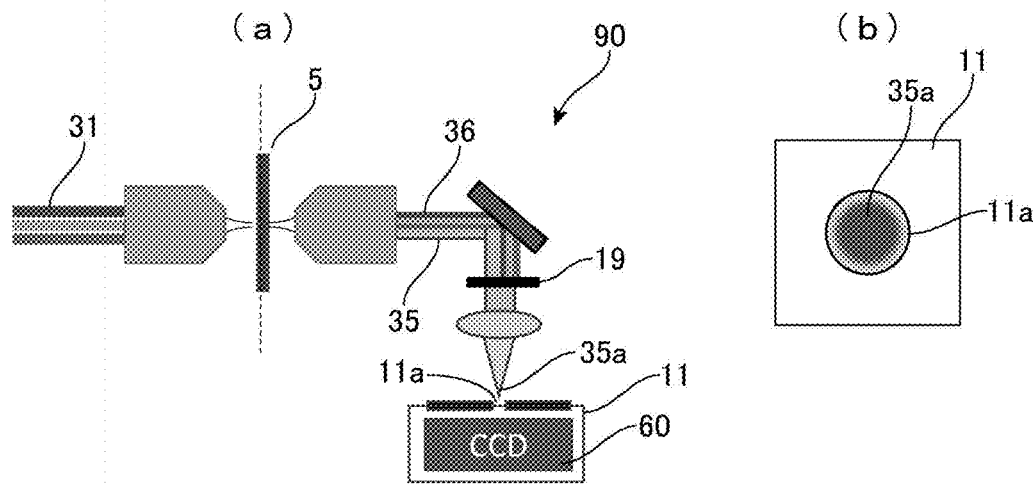
[Fig. 3]
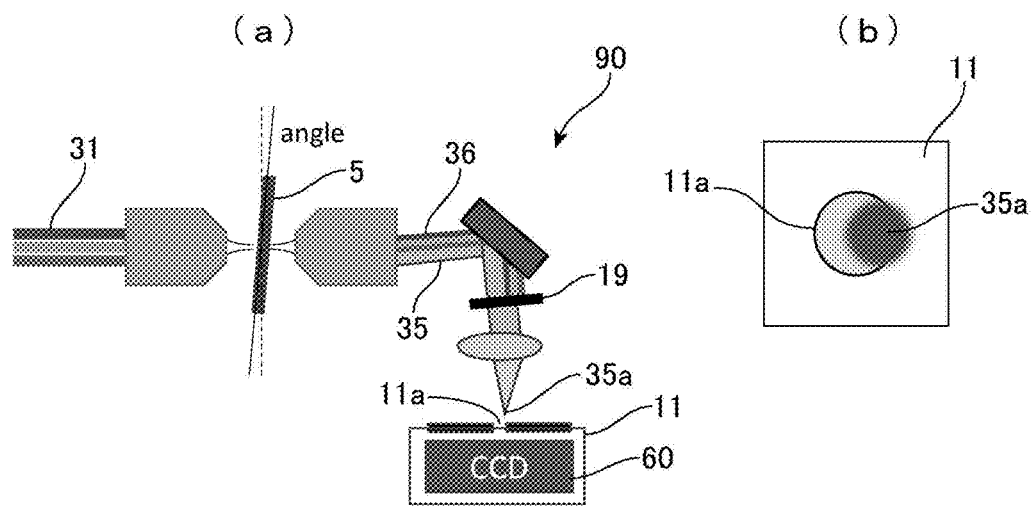
[Fig. 4]
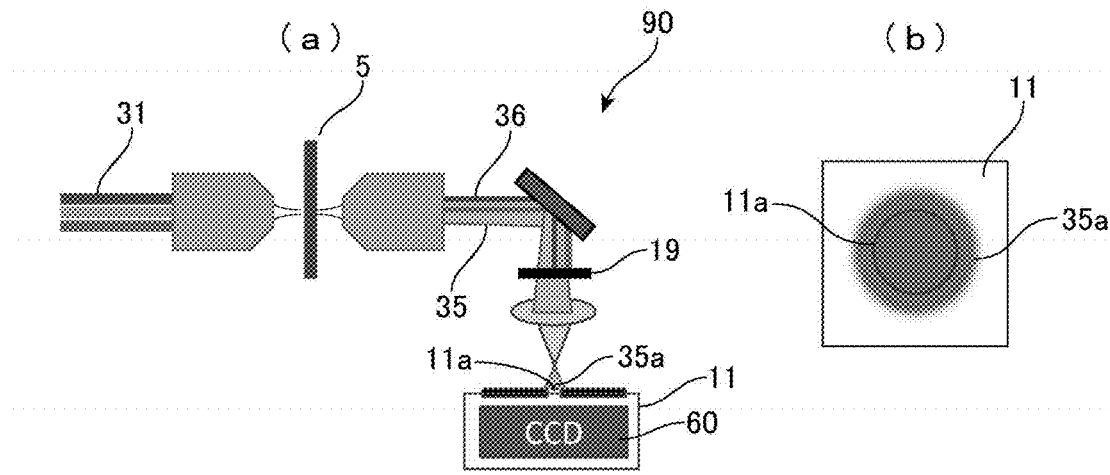

[Fig. 5]
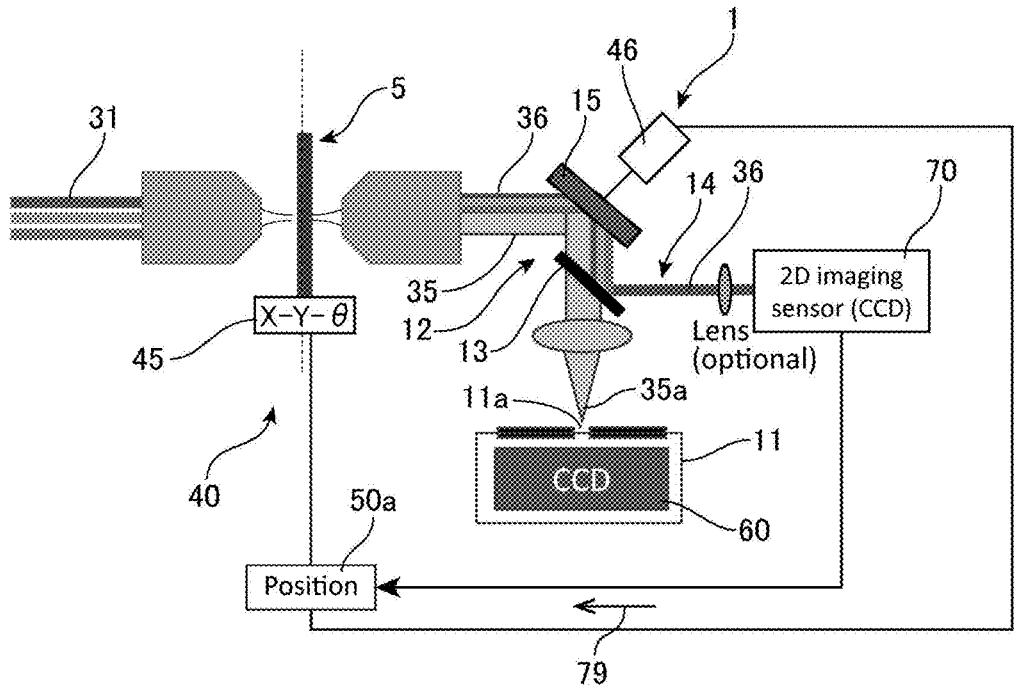
[Fig. 6]
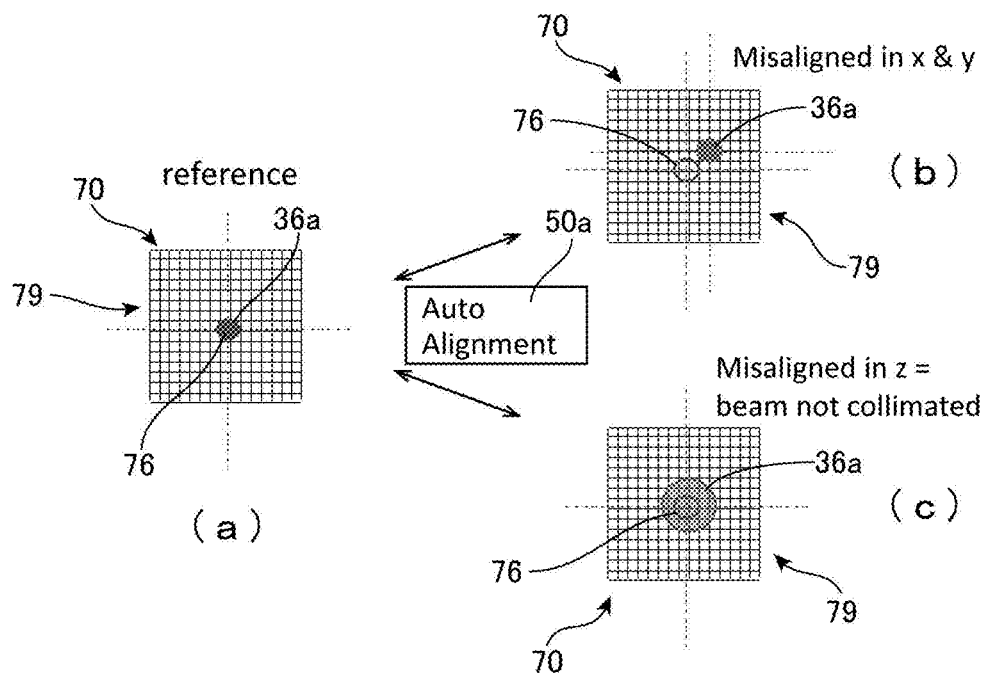

[Fig. 7]
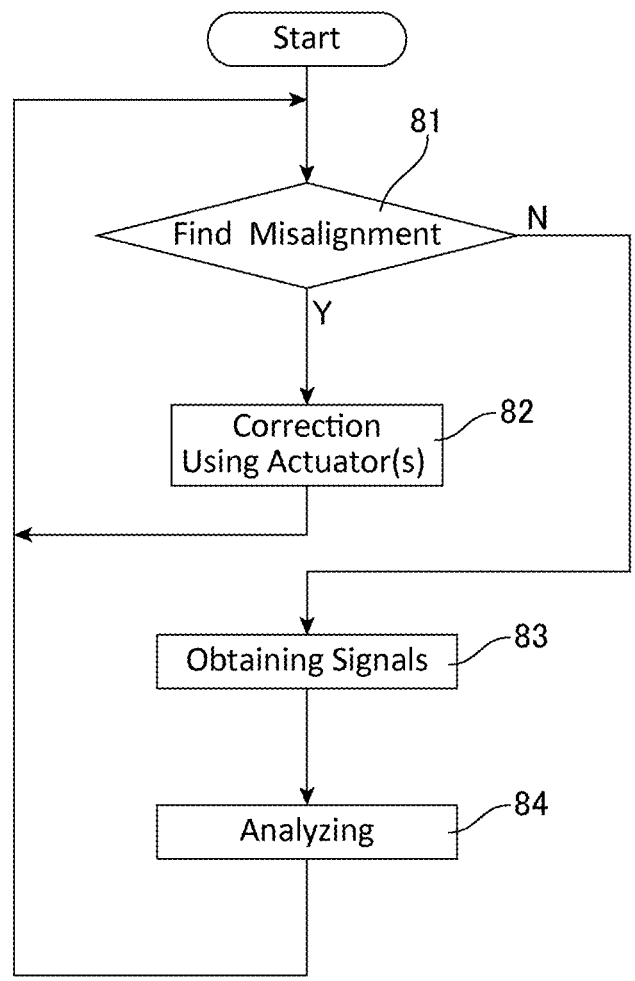

SYSTEM INCLUDING AUTO-ALIGNMENT

TECHNICAL FIELD

The invention generally relates to a system including an automatic alignment function.

BACKGROUND ART

In the publication WO2006/021929, a spectroscopic system is disclosed. In this system, by detecting the position of return radiation in a transverse plane of an aperture of a spectroscopic analysis unit, a control signal can be generated that allows to drive servo driven translation or tilting stages of optical components. In this way a transverse misalignment of a spectroscopic system can be effectively detected.

SUMMARY OF INVENTION

Detecting misalignment can be effective for efficiently detecting an emitted light (radiation) from the target (object), but using an emitted light for this purpose may reduce the intensity of the emitted light to be detected for its original purpose.

One of aspects of this invention is a system comprising a signal obtaining module for obtaining signals containing information related to components contained in a target, and a controller. The signal obtaining module includes: (a) a receiver to which an emission light generated in the target by an excitation light is input for generating the signals from the emission light; (b) a receiving optical path that guides the emission light and a residual light, which is at least a part of the excitation light propagated forward, coaxially between the target and the receiver; (c) a separator that separates the residual light from the receiving optical path to be routed to an image sensor; and (d) an actuator for controlling an optical relative position between the target and the receiver. The controller includes a module (unit) that is adapted to control the actuator to maintain an optical alignment between the target and the receiver according to a detection result of the image sensor.

In forward pass scanning optics, the target such as a cuvette or cassette sample container, in which sampling elements and materials are contained, can alter the forward optical path. When the system is set up with an initial cuvette or cassette sample container, any alteration from 90 deg may cause some refraction altering the beam path (light path, optical path). If the system is calibrated to account for an angle error, then any change in the index of refraction of the target (sample) will cause this to become misaligned. Similarly, removal and reinsertion of the sampling structure, or manufacturing tolerance of the sampling structure again will cause this to be misaligned. In the system of this invention, the optical alignment is automatically maintained using the residual light of the excitation light as a proxy for the emission light. This residual light is normally filtered out from the detection path, but in this system, the residual light, which is the light that was previously discarded, is routed to the image sensor to detect misalignment, and the alignment of the optical arrangement between the target and the receiver can be maintained by the actuator using the detection result of the image sensor.

BRIEF DESCRIPTION OF DRAWINGS

The embodiments herein will be better understood from the following detailed description with reference to the drawings, in which:

FIG. 1 shows an embodiment of a system of this invention;
FIG. 2 illustrates an example of a state of alignment;
FIG. 3 illustrates an example of misalignment;
FIG. 4 illustrates the other example of misalignment;
FIG. 5 shows a block diagram of an auto alignment system;
FIG. 6 illustrates examples of detection results;
FIG. 7 shows a flowchart of outline of control method of the system.

DESCRIPTION OF EMBODIMENTS

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

FIG. 1 illustrates a system 1 according to an embodiment of this invention. One of embodiments of the system 1 is a CARS (Coherent Anti-Stokes Raman Scattering) spectroscopy (spectroscopy analysis system, spectrometer device). In the system 1 using the nonlinear optical method such as CARS, SRS (Stimulated Raman Scattering) and others, in a target (sample, object) 5, an emission light (emission light pulse, emission beam) 35 is generated or excited by an excitation light (excitation light pulse, excitation beam, excitation laser) 31 that may include one or a plurality of lights having different wavelength ranges. The system 1 includes a laser module (generator) 20 that outputs the excitation light 31 for exciting CARS light 35 as the emission in the target 5. The excitation light 31 may include the Stokes light (Stokes pulse, Stokes beam) 32, the pump light (pump pulse, pump beam) 33 and the probe light (probe pulse, probe beam) 34 generated from a laser source 25 via the first optical path 21, the second optical path 22 and the third optical path 23 respectively.

The Stokes light 32 may have the first range R1 of wavelengths 1085-1230 nm expanded by the fiber 21a, the pump light 33 may have the second range R2 of wavelengths 1040 nm, and the probe light 34 may have the third range R3 of the wavelengths 780 nm with some delay made by the delay stage 23a. One of examples of the emission light 35 is a TD-CARS (time delayed CARS, time dependent CARS) light that has the range R4 of the wavelengths about 680-760 nm. TD-CARS light 35 is generated by the excitation light including the Stokes 32, the pump light 33 and the time delayed probe light 34. One of other examples of the emission light 35 is a CARS light that has the range R5 of the wavelengths about 900-1000 nm. The CARS light 35 is generated by the excitation light that includes the Stokes 32 and the pump light 33.

The system 1 further includes a target 5 to which the excitation light 31 is input, a target holder 45, a signal obtaining module 10, a controller (processor) 50 and a memory 53. The signal obtaining module 10 obtains signals 39 containing information related to components contained in the target 5. The signal obtaining module 10 includes a receiver 11 to which the emission light 35 generated in the target 5 by the excitation light 31 is input for generating the signals 39 from the emission light 35 for analyzing, a receiving optical path 12 that guides the emission light 35 and a residual light 36 coaxially between the target 5 and the receiver 11. The residual light 36 is at least a part of the excitation light 31 propagated forward. The signal obtaining module 10 further includes a separator 13 such as a dichroic prism or a dichroic mirror that separates the residual light 36 from the receiving optical path 12 to be routed to an image sensor 70, and an actuator 40 for controlling an optical relative position between the target 5 and the receiver 11. The controller (processing module) 50 includes a module (alignment controller) 50a that is adapted to control the actuator 40 to maintain an optical alignment between the target 5 and the receiver 11 according to a detection result of the image sensor 70. The controller 50 may include other modules such as module 50b for analyzing signals 39 detected from the emission light 35. Functions of these modules 50a and 50b may be implemented in the controller 50 using a program (program product) 53a including instructions for functioning stored in the memory (memory medium readable by a processor or a computer) 53.

The signal obtaining module 10 may include an optical path 14 that guides the separated residual light 36 to the image sensor 70. The separator 13 separates the residual light 36 from the emission light 35 and the residual light 36 coaxially input to the separator 13 on the receiving optical path 12. The separator 13 may include a dichroic separator that separates the residual light 36 from the emission light 35 by difference in their wavelengths. As explained above, by using a nonlinear optical method, the emission light (scatted light) 35 of a different wavelength than that of the excitation light 31 is obtained by the excitation light 31. For examples, the wavelength range R4 of the TD-CARS light is shorter than the range R1 to R3 of the excitation light 31 that includes the Stokes light 32, the pump light 33 and the probe light 34. The wavelength range R5 of the CARS light is shorter than the range R1 to R2 of the excitation light 31 that includes the Stokes light 32 and the pump light 33. Therefore, the separator 13 can separate the residual light 36 that has the same wavelength range of the excitation light 31 from the emission light 35. The arrangement of optical paths shown in this specification and figures are one of embodiments and the optical elements such as prisms, mirrors and lenses may be omitted or added according to actual physical conditions of the system to be realized.

One of the embodiments of the image sensor 70 is a 2D image sensor including CCD, CMOS and other imaging sensor array to be used for an image processing. The image sensor 70 may be an image processor. In the image sensor 70, the two-dimensional difference between the generated spot and the predetermined position (ideal position, reference spot) and/or the difference in the size of the spot from the ideal size (size of the reference spot) may be compared to find a misalignment.

The optical relative position controlled by the actuator 40 may include positions, orientations and/or directions of 2D (two dimensions) or 3D (three dimensions) of the optical elements such as lenses, prisms, mirrors, and their supporting plats, bases, etc., constructing and/or including the optical route or path between the target 5 and the receiver 11 in addition to the positions, orientations and/or directions of 2D or 3D of the target 5 and the receiver 11 itself. The optical alignment between the target 5 and the receiver 11, especially a receiving window 11a of the receiver 11, could be changed by changing one of elements, which include one of positions, orientations and directions of each optical element, of the optical relative position and be recovered or restored to its original state by changing another one of elements of the optical relative position. That is, in order to maintain an optical alignment, the physical position (including orientation and/or direction) of the changed element may be restored, or the physical position or positions of other elements may be changed to restore their relative optical relationship.

The actuator 40 may move at least one of a target holder 45 that holds the target 5, a supporting module 44 that supports at least a part of the receiving optical path 12 included in the signal obtaining module 10, and an optical element on the receiving optical path 12 that changes a direction of light. The actuator 40 may include a unit or units that move objects to be moved in at least two dimensions. In this system 1, the target holder 45 may be also an actuator such as an X-Y-f☐ table that can move the target 5 in 2D (two-dimensional directions) and rotate it using a servo motor, a piezoelectric actuator or the like. The target holder 45 may be an X-Y table, or an X-Y-Z-f☐ table. The supporting module 44 may be also an actuator such as an X-Y-f☐ table, an X-Y table, or an X-Y-Z-f☐ table. The receiving optical path 12 may include a prism and/or a mirror 15 that changes the direction of the received light including the emission light 35 and the residual light 36. The actuator 40 may include an actuator 46 that moves and/or rotates the mirror 15. The alignment controller 50a may control the alignment between the target 5 and the receiver 11 by individually controlling the movement and amount of movement of each actuator 44, 45 and 46.

One of examples of the receiver 11 that acquires the emission light 35, for example the CARS light or TD-CARS light, is an input lens for guiding the emission light 35 to an optical fiber for supplying the light 35 to a detector such as a spectrometer or photo detector array (CCD). The receiver 11 may also serve as the detector 60 and have a function that allows receiving the emission light 35 and outputting the detection signals 39 for analyzing the compositions of a samples in the target 5.

One of examples of the target 5 is a cuvette or a cassette sample container. When the system 1 is set up with an initial cuvette or cassette sample container, any alteration from 90 deg will cause some refraction altering the beam path including the receiving optical path 12 and the optical path 14. If the system 1 is calibrated to account for an angle error, then any change in the index of refraction of the sample in the target 5 will cause this to become misaligned. Similarly, removal and reinsertion of the sampling structure including target 5 and other elements in the optical paths of the system 1, or manufacturing tolerance of the sampling structure again will cause this to be misaligned. A detection path auto-alignment process performed by the alignment controller 50a which utilizes the residual forward propagated excitation signal (residual excitation light) 36 as a proxy for the emission signal (emission light) 35. This residual signal 36 is normally filtered out of the detection path, but in this system 1, this discarded signal is routed to a sensing element 70 that can distinguish focal diameter and XY position shifts from the reference case. This feedback is then used to drive the actuator 40 such as an adjustable mirror 15 to compensate for this shift and allow highly repeatable sampling.

FIGS. 2 to 4 illustrate the states of alignment in a conventional system 90. In this system 90, a filter 19 is installed in the upstream of the receiver 11 (detector 60) to block the residual light 36 (excitation light 31). FIG. 2 illustrates an example of perfect adjustment as shown in FIG. 2(b). A beam 35a of the emission light 35 is centered on a pinhole 11a of the receiver 11 in x-direction. The beam 35a is centered on the pinhole 11a in y-direction. A signal is collimated and perfectly focused so that the focused beam 35a enters the pinhole 11a without being (or only slightly) cut off.

FIG. 3 illustrates an example of a misalignment in x- or y-direction as shown in FIG. 3(b). A beam 35a is cut off by a pinhole 11a and decreased intensity. This misalignment may be caused by a slightly changed cuvette angle, mirror movement due to a temperature change, etc. FIG. 4 illustrates an example of a misalignment in which the beam 35a is not collimated. A signal is not perfectly focused and the beam 35a is too large. The beam 35a is larger than the pinhole 11a that causes cut off and decreased intensity. This misalignment may be caused by the different thickness of the sample, changed distance of collimation objective to sample or a sample with different refractive index, etc.

FIGS. 5 and 6 illustrate the states of alignment in this system 1. FIG. 6(a) shows an example of a detection result 79 on the 2D imaging sensor 70 corresponding to the perfect adjustment, that is, the beam 35a is centered on the pinhole 11a in x-direction and y-direction, and the signal is collimated so that the focused beam 35a enters the pinhole 11a without being (or only slightly) cut off. In such an alignment condition, the spot 36a made on the sensor 70 by the residual light 36 routed to the sensor 70 is on the reference position and the reference size of the reference spot 76.

FIG. 6(b) illustrate an example of a detection result 79 on the 2D imaging sensor 70 showing the misalignment in x- or y-direction that is corresponding to the state shown in FIG. 3. By referring to the difference of locations (x-y positions) between the reference spot 76 and the spot 36a of the residual light 36 in the detection result 79, the alignment controller (position controller) 50a can know or acquire an amount and direction of misalignment and make correction to the x and y misalignment using the actuator 40, for example an x-y table of the target holder 45 and/or the motor- or piezo-controlled mirror 15 independently or cooperatively.

FIG. 6(c) illustrates an example of a detection result 79 on the 2D imaging sensor 70 showing the misalignment in z-direction (beam not collimated) that is corresponding to the state shown in FIG. 4. By referring to the difference of spot diameters between the reference spot 76 and the spot 36a in the detection result 79, the alignment controller (position controller) 50a can know or acquire an amount and direction of misalignment and make correction to the x and y misalignment using the actuator 40, for example an x-y table of the target holder 45. As explained above, the emission light (CARS signal) 35 is collinear to input beams using the direction or pointing of the residual light (the excitation laser) 36 as proxy for the emission light (generated CARS signal) 35. A collimation change is detected by comparing to reference (measurement at beginning) and can be adjusted or corrected automatically. In addition, the separator 13 for separating the residual light 36 from the inputted light that includes the emission light 35 and residual light 36 functions as the filter 19 for blocking the excitation laser 31 of the conventional system 90.

FIG. 7 depicts a flowchart showing an overview of the process (controlling) in the system 1. In step 81, under the control of the controller 50, by acquiring the detection results 79 from the image sensor 70, the alignment controller 50a determines if there is a misalignment. In step 82, if a misalignment is found in step 81, the alignment controller 50a corrects the misalignment by controlling the actuator 40 to maintain the optical alignment between the target 5 and the receiver 11 according to the detection result 79 of the image sensor 70. In step 82, the controller 50a may move by the actuator 40 at least one of the target holder 45, the supporting module 44 and the optical element 15 independently or cooperatively.

If a misalignment is not found in step 81, in step 83, the analyzing module 50b obtains the signals for analyzing by the detector 60. In step 84, controller 50 outputs the information about the component or components of the sample in the target 5 by analyzing the signals. This process (control method) may be implemented in the controller 50 by the program (program product) 53a including the instruction stored in the memory 53 or another computer readable medium.

As explained above, in this invention, an auto beam alignment for optical detection in the spectrometer is provided. In forward pass scanning optics, sampling elements and materials contained within can alter the forward optical path. When a system is set up with an initial cuvette or cassette sample container, any alteration from 90 deg will cause some refraction altering the beam path. If a system is calibrated to account for an angle error, then any change in the index of refraction of the sample will cause this to become misaligned. Similarly, removal and reinsertion of the sampling structure, or manufacturing tolerance of the sampling structure again will cause this to be misaligned. We have developed a detection path auto-alignment process which utilizes the residual forward propagated excitation signal as a proxy for the emission signal. This residual signal is normally filtered out of the detection path, but in our case, this discarded signal is routed to a sensing element that can distinguish focal diameter and XY position shifts from the reference case. This feedback is then used to drive an adjustable mirror to compensate for this shift and allow highly repeatable sampling.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

The invention claimed is:
1. A system comprising:
an input optical path configured to input an excitation light to a target to generate an emission light containing information related to components contained in the target using a nonlinear optical method;
a signal obtaining module for obtaining signals containing the information related to the components contained in the target from the emission light propagated forward through the target; and
a controller,
wherein the signal obtaining module includes:
a detector to which the emission light is input for generating the signals from the emission light;
a receiving optical path that guides the emission light and a residual light, which is at least a part of the excitation light propagated forward through the target with the emission light, coaxially between the target and the detector;

a separator that separates the residual light from the receiving optical path to be routed to an image sensor;

an optical path that guides the separated residual light to the image sensor; and an actuator for controlling an optical relative position between the target and the detector, and the controller includes a module that is adapted to control the actuator to maintain an optical alignment between the target and the detector that detects the emission light filtered by the separator according to a detection result of the separated residual light on the image sensor.

2. The system according to claim 1, wherein the actuator moves at least one of a target holder that holds the target, a supporting module that supports at least a part of the receiving optical path, and an optical element on the receiving optical path that changes a direction of light.

3. The system according to claim 1, wherein the actuator includes a unit that moves an object to be moved in at least two dimensions.

4. The system according to claim 1, wherein the separator includes a separator that separates the residual light from the emission light by difference in their wavelengths.

5. The system according to claim 1, further comprising:
a generator configured to generate the excitation light; and
a spectrometer configured to acquire spectra of the emission light received on the detector.

6. The system according to claim 1, wherein the nonlinear optical method is CARS.

7. The system according to claim 1, wherein the nonlinear optical method is SRS.

8. A method of controlling a system comprising:
an input optical path configured to input an excitation light to a target to generate an emission light containing information related to components contained in the target using a nonlinear optical method, and
a signal obtaining module for obtaining signals containing the information related to the components contained in a target from the emission light propagated forward through the target,
wherein the signal obtaining module includes:
a detector to which the emission light is input for generating the signals from the emission light;
a receiving optical path that guides the emission light and a residual light, which is at least a part of the excitation light propagated forward through the target with the emission light, coaxially between the target and the detector;
a separator that separates the residual light from the receiving optical path and directs the residual light to an image sensor;
an optical path that guides the separated residual light to the image sensor; and
an actuator for controlling an optical relative position between the target and the detector, and
the method includes controlling the actuator to maintain an optical alignment between the target and the detector that detects the emission light filtered by the separator according to a detection result of the separated residual light on the image sensor.

9. The method according to claim 8, wherein the controlling includes moving by the actuator at least one of a target holder that holds the target, a supporting module that supports at least a part of the receiving optical path, and an optical element on the receiving optical path that changes a direction of light.

10. The method according to claim 8, wherein the nonlinear optical method is CARS.

11. The method according to claim 8, wherein the nonlinear optical method is SRS.

12. A program product for controlling a system comprising:
an input optical path configured to input an excitation light to a target to generate an emission light containing information related to components contained in the target using a nonlinear optical method, and
a signal obtaining module for obtaining signals containing the information related to the components contained in a target from the emission light propagated forward through the target,
wherein the signal obtaining module includes:
a detector to which the emission light is input for generating the signals from the emission light;
a receiving optical path that guides the emission light and a residual light, which is at least a part of the excitation light propagated forward through the target with the emission light, coaxially between the target and the detector;
a separator that separates the residual light from the receiving optical path and directs the residual light to an image sensor;
an optical path that guides the separated residual light to the image sensor; and
an actuator for controlling an optical relative position between the target and the detector, and
the program includes instructions of a controller for controlling the actuator to maintain an optical alignment between the target and the detector that detects the emission light filtered by the separator according to a detection result of the separated residual light on the image sensor.

13. The program product according to claim 12, wherein the nonlinear optical method is CARS.

14. The program product according to claim 12, wherein the nonlinear optical method is SRS.

* * * * *